US005580767A

United States Patent [19]

Cowsert et al.

[11] Patent Number: 5,580,767

[45] Date of Patent: Dec. 3, 1996

[54] INHIBITION OF INFLUENZA VIRUSES BY ANTISENSE OLIGONUCLEOTIDES

[75] Inventors: Lex M. Cowsert; David J. Ecker, both of Carlsbad, Calif.

[73] Assignee: Isis Pharmaceuticals, Inc., Carlsbad, Calif.

[21] Appl. No.: 955,718

[22] PCT Filed: Aug. 13, 1991

[86] PCT No.: PCT/US91/05742

§ 371 Date: Sep. 22, 1992

§ 102(e) Date: Sep. 22, 1992

[87] PCT Pub. No.: WO92/03454

PCT Pub. Date: Mar. 5, 1992

Related U.S. Application Data

[63] Continuation-in-part of Ser. No. 567,287, Aug. 14, 1990, abandoned.

[51] Int. Cl.[6] .......... C12N 15/00; C07H 21/04

[52] U.S. Cl. .......... 435/172.3; 536/24.5

[58] Field of Search .......... 514/44; 536/24.5; 435/238

[56] References Cited

U.S. PATENT DOCUMENTS

| | | |
|---|---|---|
| 4,689,320 | 8/1987 | Kaji . |
| 5,004,810 | 4/1991 | Draper et al. . |
| 5,166,195 | 11/1992 | Ecker et al. . |
| 5,194,428 | 3/1993 | Agrawal . |

FOREIGN PATENT DOCUMENTS

| | | |
|---|---|---|
| 82110494 | 6/1983 | European Pat. Off. . |
| 169787 | 1/1986 | European Pat. Off. . |

OTHER PUBLICATIONS

Silva et al (1994) Mol. Pharmocol. 46, 51–57.

Morishita et al (1993) Proced. Natl. Acad. Sci. 90, 8474–8478.

Ratojczak et al (1992) Proc. Natl Acad. Sci 89,11823–11827.

Whitesell et al (1991) Antisense Res. & Develop. 1, 343–350.

Trierr, et al (1993) Biochem Bioph Res. Comm. 190, 952–960.

Bunnell et al (1992) Somat. Cell Molec. Gen. 18, 559–569.

Offensperger et al (1993) EMBO J. 12, 1257–1262.

Simons et al (1992) Nature 359, 67–70.

Cox et al (1988) Virology 167, 554–567.

Burch et al (1991) Clin. Invest. 88, 1190–1196.

Kitajima et al (1992) Science 258, 1792–1795.

Higgins et al (1993) Proced. Natl. Acad. Sci. 90, 9901–9905.

Cohen et al (1994) Sci. Am., Dec., 76–82.

Agrawal et al (1991) Adv. Drug. Delv. Rev. 6, 251–270.

Erlich et al., Searching for Antiviral Materials from Microbial Fermentations, *Ann. N.Y. Acad. Sci.* 1965, 130:5–16.

Mossman, T., Rapid Colorimetric Assay for Cellurlar Growth and Survival: Application and Proliferation and Cytotoxicity Assays, *J. Immunol. Methods,* 1983 65:55.

Douglas, R. G., Prophylaxis and Treatment of Influenza, *New England Journal of Medicine,* 1990 322:443–450.

Leiter, J. et al., Inhibition of influenza virus replication by phosphorothioate oligodeoxynucleotides, *Proc. Natl. Acad. Sci. USA,* 87:3430–3434 1990.

Zerial, A. et al., Selective inhiibtion of the cytopathic effect of type A influenza viruses by oligodeoxynucleotides covalently linked to an intercalating agent, *Nucleic Acids Res.,* 15:9909–9919 1987.

Kavanov, A. V. et al., A new class of antivirals: antisense oligonucleotides combined with a hydrophobic substituent effectively inhibit influenza virus reproduction and synthesis of virus–specific proteins in MDCK cells, *FEBS,* 259:327–330 1990.

Rothenberg et al., Oligodeoxynucleotide as Anti–sense Inhibitors of Gene Expression: Therapeutic Implications, *J. Natl. Cancer Inst.,* 81:1539–1544 1989.

Zon, G., Oligonucleotide Analogues as Potential Chemotherapeutic Agents, *Pharmaceutical Res.,* 5:539–549 1988.

Yisraeli et al., Synthesis of Long, Capped Transcripts in Vitro by SP6 and T7 RNA Polymerases, *Methods in Enzymology,* 180:42–50 1989.

Sanger, F. et al., DNA sequencing with chain–terminating inhibitors, *Proc. Natl, Acad. Sci.,* 74:5463–5467 1977.

*Primary Examiner*—Jacqueline M. Stone

*Assistant Examiner*—Deborah Crouch

*Attorney, Agent, or Firm*—Law Offices of Jane Massey Licata

[57] ABSTRACT

Compositions and methods are provided for the treatment and diagnosis of influenza virus infections. In accordance with preferred embodiments, oligonucleotides and oligonucleotide analogs are provided which are specifically hybridizable with viral RNAs. The oligonucleotide comprises nucleotide units sufficient in identity and number to effect said specific hybridization. In other preferred embodiments, the oligonucleotides are specifically hybridizable with a transcription initiation site, a translation initiation site, 5'-untranslated sequences, 3'-untranslated sequences, and intron/exon junction of influenza virus mRNAs. In additional preferred embodiments, the oligonucleotides are specifically hybridizable with RNA sequences involved in splicing of the viral RNA, or in viral packaging. Methods of treating animals suffering from influenza virus infection are disclosed.

4 Claims, 9 Drawing Sheets

1 AGCAAAAGCA GGGUAGAUAA UCACUCACUG AGUGACAUCA AAAUCAUGGC

51 GUCCCAAGGC ACCAAACGGU CUUAUGAACA GAUGGAAACU GAUGGGGAAC

101 GCCAGAAUGC AACUGAAAUC AGAGCAUCCG UCGGGAAGAU GAUUGAUGGA

151 AUUGGACGAU UCUACAUCCA AAUGUGCACC GAACUUAAAC UCAGUGAUUA

201 UGAGGGGCGG CUGAUCCAGA ACAGCUUAAC AAUAGAGAGA AUGGUGCUCU

251 CUGCUUUUGA CGAGAGGAGG AAUAAAUAUC UGGAAGAACA UCCCAGCGCG

301 GGGAAGGAUC CUAAGAAAAC UGGAGGACCC AUAUACAAGA GAGUAGAUGG

351 AAAGUGGAUG AGGGAACUCG UCCUUUAUGA CAAAGAAGAA AUAAGGCGAA

401 UCUGGCGCCA AGCUAAUAAU GGUGAUGAUG CAACAGCUGG UCUGACUCAC

451 AUGAUGAUCU GGCAUUCCAA UUUGAAUGAU ACAACAUACC AGAGGACAAG

501 AGCUCUUGUU CGCACCGGAA UGGAUCCCAG GAUGUGCUCU UUGAUGCAGG

551 GUUCGACUCU CCCUAGGAGG UCUGGAGCCG CAGGCGCUGC AGUCAAAGGA

601 GUUGGGACAA UGGUGAUGGA GUUGAUAAGG AUGAUCAAAC GUGGGAUCAA

651 UGAUCGGAAC UUCUGGAGAG GUGAGAAUGG GCGGAAAACA AGGAAUGCUU

701 AUGAGAGAAU GUGCAACAUU CUCAAAGGAA AAUUUCAAAC AGCUGCACAA

751 AGAGCAAUGA UGGAUCAAGU GAGAGAAAGC CGGAACCCAG GAAAUGCUGA

801 GAUCGAAGAU CUCAUCUUUC UGGCACGGUC UGCACUCAUA UUGAGAGGGU

851 CAGUUGCUCA CAAAUCUUGU CUGCCUGCCU GUGUGUAUGG ACCUGCCGUA

901 GCCAGUGGCU ACGACUUCGA AAAAGAGGGA UACUCUUUAG UAGGGAUAGA

951 CCCUUUCAAA CUGCUUCAAA ACAGCCAAGU AUACAGCCUA AUCAGACCGA

1001 AUGAGAAUCC AGCACACAAG AGUCAGCUGG UGUGGAUGGC AUGCAAUUCU

1051 GCUGCAUUUG AAGAUCUAAG AGUAUCAAGC UUCAUCAGAG GGACCAAAGU

1101 AAUCCCAAGG GGGAAACUUU CCACUAGAGG AGUACAAAUU GCUUCAAAUG

1151 AAAACAUGGA UACUAUGGGA UCAAGUACUC UUGAACUGAG AAGCAGGUAC

1201 UGGGCCAUAA GGACCAGAAG UGGAGGAAAC ACUAAUCAAC AGAGGGCCUC

1251 UGCAGGUCAA AUCAGUGUAC AACCUACGUU UUCUGUGCAA AGAAACCUCC

Fig. 1a

```
1301  CAUUUGACAA ACCAACCAUC AUGGCAGCAU UCACUGGGAA UGCAGAGGGA
1351  AGAACAUCAG ACAUGAGGGC AGAAAUCAUA AGGAUGAUGG AAGGUGCAAA
1401  ACCAGAAGAA GUGUCCUUCC AGGGGCGGGG AGUCUUCGAG CUCUCGGACG
1451  AAAAGGCAAC GAACCCGAUC GUGCCCUCUU UUGACAUGAG UAAUGAAGGA
1501  UCUUAUUUCU UCGGAGACAA UGCAGAGGAG UACGACAAUU AAGGAAAAAN
1551  UACCCUUGUU UCUACU
```

Fig. 1b

1 UCGUUUUCGU CCCAUCUAUU AGUGAGUGAC UCACUGUAGU UUUAGUACCG
51 CAGGGUUCCG UGGUUUGCCA GAAUACUUGU CUACCUUUGA CUACCCCUUG
101 CGGUCUUACG UUGACUUUAG UCUCGUAGGC AGCCCUUCUA CUAACUACCU
151 UAACCUGCUA AGAUGUAGGU UUACACGUGG CUUGAAUUUG AGUCACUAAU
201 ACUCCCCGCC GACUAGGUCU UGUCGAAUUG UUAUCUCUCU UACCACGAGA
251 GACGAAAACU GCUCUCCUCC UUAUUUAUAG ACCUUCUUGU AGGGUCGCGC
301 CCCUUCCUAG GAUUCUUUUG ACCUCCUGGG UAUAUGUUCU CUCAUCUACC
351 UUUCACCUAC UCCCUUGAGC AGGAAAUACU GUUUCUUCUU UAUUCCGCUU
401 AGACCGCGGU UCGAUUAUUA CCACUACUAC GUUGUCGACC AGACUGAGUG
451 UACUACUAGA CCGUAAGGUU AAACUUACUA UGUUGUAUGG UCUCCUGUUC
501 UCGAGAACAA GCGUGGCCUU ACCUAGGGUC CUACACGAGA AACUACGUCC
551 CAAGCUGAGA GGGAUCCUCC AGACCUCGGC GUCCGCGACG UCAGUUUCCU
601 CAACCCUGUU ACCACUACCU CAACUAUUCC UACUAGUUUG CACCCUAGUU
651 ACUAGCCUUG AAGACCUCUC CACUCUUACC CGCCUUUUGU UCCUUACGAA
701 UACUCUCUUA CACGUUGUAA GAGUUUCCUU UUAAAGUUUG UCGACGUGUU
751 UCUCGUUACU ACCUAGUUCA CUCUCUUUCG GCCUUGGGUC CUUUACGACU
801 CUAGCUUCUA GAGUAGAAAG ACCGUGCCAG ACGUGAGUAU AACUCUCCCA
851 GUCAACGAGU GUUUAGAACA GACGGACGGA CACACAUACC UGGACGGCAU
901 CGGUCACCGA UGCUGAAGCU UUUUCUCCCU AUGAGAAAUC AUCCCUAUCU
951 GGGAAAGUUU GACGAAGUUU UGUCGGUUCA UAUGUCGGAU UAGUCUGGCU
1001 UACUCUUAGG UCGUGUGUUC UCAGUCGACC ACACCUACCG UACGUUAAGA
1051 CGACGUAAAC UUCUAGAUUC UCAUAGUUCG AAGUAGUCUC CCUGGUUUCA
1101 UUAGGGUUCC CCCUUUGAAA GGUGAUCUCC UCAUGUUUAA CGAAGUUUAC
1151 UUUUGUACCU AUGAUACCCU AGUUCAUGAG AACUUGACUC UUCGUCCAUG
1201 ACCCGGUAUU CCUGGUCUUC ACCUCCUUUG UGAUUAGUUG UCUCCCGGAG
1251 ACGUCCAGUU UAGUCACAUG UUGGAUGCAA AAGACACGUU UCUUUGGAGG

*Fig. 2a*

1301 GUAAACUGUU UGGUUGGUAG UACCGUCGUA AGUGACCCUU ACGUCUCCCU

1351 UCUUGUAGUC UGUACUCCCG UCUUUAGUAU UCCUACUACC UUCCACGUUU

1401 UGGUCUUCUU CACAGGAAGG UCCCCGCCCC UCAGAAGCUC GAGAGCCUGC

1451 UUUUCCGUUG CUUGGGCUAG CACGGGAGAA AACUGUACUC AUUACUUCCU

1501 AGAAUAAAGA AGCCUCUGUU ACGUCUCCUC AUGCUGUUAA UUCCUUUUUN

1551 AUGGGAACAA AGAUGA

*Fig. 2b*

```
   1  AGCAAAAGCA GGUAGAUAUU GAAAGAUGAG UCUUCUAACC GAGGUCGAAA
  51  CGUACGUUCU CUCUAUCAUC CCGUCAGGCC CCCUCAAAGC CGAGAUCGCA
 101  CAGAGACUUG AAGAUGUCUU UGCUGGGAAA AACACCGAUC UUGAGGCUCU
 151  CAUGGAAUGG CUAAAGACAA GACCAAUCCU GUCACCUCUG ACUAAGGGGA
 201  UUUUGGGAUU UGUAUUCACG CUCACCGUGC CCAGUGAGCG AGGACUGCAG
 251  CGUAGACGCU UUGUCCAAAA UGCCCUCAAU GGGAAUGGGG AUCCAAAUAA
 301  CAUGGACAGA GCAGUUAAAC UGUAUAGAAA GCUUAAGAGG GAGAUAACAU
 351  UCCAUGGGGC CAAAGAAAUA GCGCUCAGUU AUUCUGCUGG UGCACUUGCC
 401  AGUUGUAUGG GCCUCAUAUA CAACAGGAUG GGGGCUGUGA CCACUGAAGU
 451  GGUCUUAGGC CUGGUAUGUG CAACCUGUGA ACAGAUUGCU GACUCCCAGC
 501  AUAGGUCUCA UAGGCAAAUG GUGACAACAA CCAAUCCACU AAUAAGACAU
 551  GAGAACAGAA UGGUUCUGGC CAGCACUACA GCUAAGGCUA UGGAGCAAAU
 601  GGCUGGAUCG AGUGAGCAAG CAGCAGAGGC CAUGGAGGUU GCUAGUCAGG
 651  CCAGGCAAAU GGUGCAGGCA AUGAGAGUUA UUGGGACUCA UCCUAGCUCC
 701  AGUGCUGGUC UAAAAAAUGA UCUUCUUGAA AAUUUGCAGG CCUAUCAGAA
 751  ACGAAUGGGG GUGCAGAUGC AACGAUUCAA GUGACCCUCU UGUUGUUGCC
 801  GCGAGUAUCA UUGGGAUCUU GCACUUGAUA UUGUGGAUUC UUGAUCAUCU
 851  UUUUUUCAAA UGCAUUUAUC GCUUCUUUAA ACACGGUCUG AAAAGAGGGC
 901  CUUCUACGGA AGGAGUACCA GAGUCUAUGA GGGAAGAAUA UCGAAAGGAA
 951  CAGCAGAGUG CUGUGGAUGC UGACGAUAGU CAUUUUGUCA GCAUAGAGCU
1001  GGAGUAAAAA ACUACCUUGU UUCUACU
```

Fig. 3

1 UCGUUUUCGU CCAUCUAUAA CUUUCUACUC AGAAGAUUGG CUCCAGCUUU
51 GCAUGCAAGA GAGAUAGUAG GGCAGUCCGG GGGAGUUUCG GCUCUAGCGU
101 GUCUCUGAAC UUCUACAGAA ACGACCCUUU UUGUGGCUAG AACUCCGAGA
151 GUACCUUACC GAUUUCUGUU CUGGUUAGGA CAGUGGAGAC UGAUUCCCCU
201 AAAACCCUAA ACAUAAGUGC GAGUGGCACG GGUCACUCGC UCCUGACGUC
251 GCAUCUGCGA AACAGGUUUU ACGGGAGUUA CCCUUACCCC UAGGUUUAUU
301 GUACCUGUCU CGUCAAUUUG ACAUAUCUUU CGAAUUCUCC CUCUAUUGUA
351 AGGUACCCCG GUUUCUUUAU CGCGAGUCAA UAAGACGACC ACGUGAACGG
401 UCAACAUACC CGGAGUAUAU GUUGUCCUAC CCCCGACACU GGUGACUUCA
451 CCAGAAUCCG GACCAUACAC GUUGGACACU UGUCUAACGA CUGAGGGUCG
501 UAUCCAGAGU AUCCGUUUAC CACUGUUGUU GGUUAGGUGA UUAUUCUGUA
551 CUCUUGUCUU ACCAAGACCG GUCGUGAUGU CGAUUCCGAU ACCUCGUUUA
601 CCGACCUAGC UCACUCGUUC GUCGUCUCCG GUACCUCCAA CGAUCAGUCC
651 GGUCCGUUUA CCACGUCCGU UACUCUCAAU AACCCUGAGU AGGAUCGAGG
701 UCACGACCAG AUUUUUUACU AGAAGAACUU UUAAACGUCC GGAUAGUCUU
751 UGCUUACCCC CACGUCUACG UUGCUAAGUU CACUGGGAGA ACAACAACGG
801 CGCUCAUAGU AACCCUAGAA CGUGAACUAU AACACCUAAG AACUAGUAGA
851 AAAAAAGUUU ACGUAAAUAG CGAAGAAAUU UGUGCCAGAC UUUUCUCCCG
901 GAAGAUGCCU UCCUCAUGGU CUCAGAUACU CCCUUCUUAU AGCUUUCCUU
951 GUCGUCUCAC GACACCUACG ACUGCUAUCA GUAAAACAGU CGUAUCUCGA
1001 CCUCAUUUUU UGAUGGAACA AAGAUGA

*Fig. 4*

1 AGCAAAAGCA GGGUGACAAA GACAUAAUGG AUCCUAACAC UGUGUCAAGC
51 UUUCAGGUAG AUUGCUUCCU UUGGCAUGUC CGCAAACAAG UUGCAGACCA
101 AGAACUAGGU GAUGCCCCAU UCCUUGAUCG GCUUCGCCGA GAUCAGAAGU
151 CCCUAAGGGG AAGAGGCAGU ACUCUCGGUC UGAACAUCGA AACAGCCACC
201 CGUGUUGGAA AGCAGAUAGU GGAGAGGAUU CUGAAGGAAG AAUCCGAUGA
251 GGCACUUAAA AUGACCAUGG CCUCCGCACC UGCUUCGCGA UACCUAACUG
301 ACAUGACUAU UGAGGAAAUG UCAAGGGACU GGUUCAUGCU AAUGCCCAAG
351 CAGAAAGUGG CAGGCCCUCU UUGUAUCAGA AUGGACCAGG CAAUCAUGGA
401 UAAGAACAUC AUAUUGAAAG CGAAUUUCAG UGUGAUUUUU GACCGGCUAG
451 AGACCCUAAU AUUACUAAGG GCUUUCACCG AAGCGGGAGC AAUUGUUGGC
501 GAAAUUUCAC CAUUGCCUUC UCUUCCAGGA CAUACUAAUG AGGAUGUCAA
551 AAAUGCAAUU GGGGUCCUCA UCGGAGGACU UGAAUGGAAU GAUAACACAG
601 UUCGAGUCUC UAAAACUCUA CAGAGAUUCG CUUGGAGAAG CAGUGAUGAG
651 AAUGGGAGAC CUCCACUCAC UCCAAAAUAG AAACGGAAAA UGGCGAGAAC
701 AAUUAGGUCA AAAGUUCGAA GAAAUAAGAU GGCUGAUUGA AGAAGUGAGA
751 CACAAAUUGA AGAUAACAGA GAAUAGUUUU GAGCAAAUAA CAUUUAUGCA
801 AGCCUUACAG CUACUAUUUG AAGUGGAACA AGAGAUAAGA ACUUUCUCGU
851 UUCAGCUUAU UUAAUGAUAA AAAACACCCU UGUUUCUACU

*Fig. 5*

```
1   UCGUUUUCGU CCCACUGUUU CUGUAUUACC UAGGAUUGUG ACACAGUUCG
51  AAAGUCCAUC UAACGAAGGA AACCGUACAG GCGUUUGUUC AACGUCUGGU
101 UCUUGAUCCA CUACGGGGUA AGGAACUAGC CGAAGCGGCU CUAGUCUUCA
151 GGGAUUCCCC UUCUCCGUCA UGAGAGCCAG ACUUGUAGCU UUGUCGGUGG
201 GCACAACCUU UCGUCUAUCA CCUCUCCUAA GACUUCCUUC UUAGGCUACU
251 CCGUGAAUUU UACUGGUACC GGAGGCGUGG ACGAAGCGCU AUGGAUUGAC
301 UGUACUGAUA ACUCCUUUAC AGUUCCCUGA CCAAGUACGA UUACGGGUUC
351 GUCUUUCACC GUCCGGGAGA AACAUAGUCU UACCUGGUCC GUUAGUACCU
401 AUUCUUGUAG UAUAACUUUC GCUUAAAGUC ACACUAAAAA CUGGCCGAUC
451 UCUGGGAUUA UAAUGAUUCC CGAAAGUGGC UUCGCCCUCG UUAACAACCG
501 CUUUAAAGUG GUAACGGAAG AGAAGGUCCU GUAUGAUUAC UCCUACAGUU
551 UUUACGUUAA CCCCAGGAGU AGCCUCCUGA ACUUACCUUA CUAUUGUGUC
601 AAGCUCAGAG AUUUUGAGAU GUCUCUAAGC GAACCUCUUC GUCACUACUC
651 UUACCCUCUG GAGGUGAGUG AGGUUUUAUC UUUGCCUUUU ACCGCUCUUG
701 UUAAUCCAGU UUUCAAGCUU CUUUAUUCUA CCGACUAACU UCUUCACUCU
751 GUGUUUAACU UCUAUUGUCU CUUAUCAAAA CUCGUUUAUU GUAAAUACGU
801 UCGGAAUGUC GAUGAUAAAC UUCACCUUGU UCUCUAUUCU UGAAAGAGCA
851 AAGUCGAAUA AAUUACUAUU UUUUGUGGGA ACAAAGAUGA
```

Fig. 6

INHIBITION OF INFLUENZA VIRUSES BY ANTISENSE OLIGONUCLEOTIDES

This is a continuation-in-part application of parent application Ser. No. 567,287, filed Aug. 14, 1990, now abandoned.

FIELD OF THE INVENTION

This invention relates to diagnostics, research reagents, and therapies for influenza virus infections. In particular, this invention relates to antisense oligonucleotide interactions with certain viral ribonucleic acids and messenger ribonucleic acids involved in the infection of cells by influenza viruses. Oligonucleotides are provided which hybridize to the viral RNA segments of influenza viruses or to certain mRNA's which encode the NP, M1, M2, NS1, NS2 or other key proteins of influenza viruses, including RNA polymerase, hemagglutinin, nucleoprotein or neuraminidase. Oligonucleotides are also provided which hybridize to certain viral RNA sequences important for RNA splicing or for viral packaging. These oligonucleotides have been found to lead to the modulation of the activity of the RNA; modulation of infection, diagnosis, palliation or therapeutic effect result.

BACKGROUND OF THE INVENTION

Influenza viruses have been a major cause of mortality and morbidity in man throughout recorded history. Epidemics occur at regular intervals which vary widely in severity but which always cause significant mortality and morbidity, most frequently in the elderly population. The cause of influenza epidemics was first attributed to a virus by R. E. Shops, who showed that influenza epidemics could be transmitted with filtered mucus. Influenza viruses are currently divided into three types: A, B, and C, based upon differences in internal antigenic proteins.

An influenza infection produces an acute set of symptoms including headache, cough, fever and general malaise. In severe cases or situations involving pre-existing pulmonary or cardiovascular disease, hospitalization is required. Pneumonia due to direct viral infection or due to secondary bacterial or viral invasion is the most frequent complication. For a review on the clinical aspects of influenza virus infection see Douglas, R. G., *New England Journal of Medicine,* 322:443–450 (1990).

New strains of influenza caused by antigenic drift appear at regular frequency, usually annually, and begin a cycle of infection which travels around the globe. Little is known about how individual epidemics are initiated. Major new subtypes of influenza appear less frequently but can result in major pandemics.

The most effective way to deal with the influenza virus for the population at risk of severe complications is by prevention. Use of the available influenza vaccine is an effective way to lower the mortality in a population, however due to the ever-changing nature of the virus, the development of a vaccine with the appropriate composition to protect against the currently circulating virus strains is complex and expensive. Moreover, patient compliance in receiving the vaccine is generally very low. Thus large numbers of patients at risk of serious complications from influenza virus go unprotected.

There are several drugs available which have some activity against the influenza virus prophylactically. None, however, are effective against influenza type B. Moreover, they are generally of very limited use therapeutically, and have not been widely used in treating the disease after the onset of symptoms. Accordingly, there is a world-wide need for improved therapeutic agents for the treatment of influenza virus infections.

Prior attempts at the inhibition of influenza virus using antisense oligonucleotides have been reported. Leiter and co-workers have targeted phosphodiester and phosphorothioate oligonucleotides to influenza A and influenza C viruses. Leiter, J., Agrawal, S., Palese, P. & Zamecnik, P. C., *Proc. Natl. Acad. Sci. USA,* 87:3430–3434(1990). These workers targeted only the polymerase PB1 gene and mRNA in the vRNA 3' region and mRNA 5' region, respectively. Sequence-specific inhibition of influenza A was not observed although some specific inhibition of influenza C was noted. No other influenza virus segments or mRNA's were targeted.

Zerial and co-workers have reported inhibition of influenza A virus by oligonucleotides coincidentally linked to an intercalating agent. Zerial, A., Thuong, N. T. & Helene, C., *Nucleic Acids Res.,* 57:9909–9919 (1987). Zerial et al. targeted the 3' terminal sequence of 8 vRNA segments. Their oligonucleotide analog was reported to inhibit the cytopathic effects of the virus in cell culture. EP Patent 169787, Helene et al. disclose oligonucleotide compounds covalently bound to an intercalating group and complementary with a nucleic acid sequence involved in replication of a nucleic acid and of transcription and/or translation of one or more genes; oligonucleotides covalently bound to an intercalating group and complementary with a sequence for replicating or developing a virus or bacterium or parasite; and oligonucleotides covalently bound to an intercalating group and complementary with a sequence for replicating or developing the influenza or herpes virus, or with an oncogene.

European Patent Application No. 82110494.0 (Krug et al.) discloses oligonucleotides containing a 5' methylated cap structure to increase the affinity of the oligonucleotide for influenza viral endonuclease and transcriptase. In addition, capped oligonucleotides are modified to prevent them from acting as primers, e.g., being less than 10 nucleotides in length; or extended to contain a 3' terminal deoxymononucleotide or a 3' terminal 3'-O-methylated ribonucleotide; or having at least 14 nucleotides modified in the sugar and/or base moieties and/or in the nucleotide bond.

Kabanov and co-workers have synthesized an oligonucleotide complementary to the loop-forming site of RNA encoding RNA polymerase 3. Kabanov, A. V., Vinogradov, S. V., Ovcharenko, A. V., Krivonos, A. V., Melik-Nubarov, N. S., Kiselev, V. I. & Severin, E. S., *FEBS,* 259:327–330 (1990). Their oligonucleotide was conjugated to a undecyl residue at the 5' terminal phosphate group. They found that their oligonucleotide inhibited influenza A virus infection in MDCK cells.

Although each of the foregoing workers reported some degree of success in inhibiting some function of an influenza virus, a general therapeutic scheme to target influenza viruses has not been found. Moreover, improved efficacy is required in influenza virus therapeutics. Accordingly, there has been and continues to be a long-felt need for the design of antisense oligonucleotide analogs which are capable of effective therapeutic use. This long-felt need has not been satisfied by prior work in the field of antisense oligonucleotide therapy for influenza. Others have failed to identify target sites in which antisense oligonucleotides or oligonucleotide analogs are therapeutically effective at reasonable rates of application.

OBJECTS OF THE INVENTION

It is a principle object of the invention to provide therapies for influenza virus infections in animals, especially in man.

It is a further object of the invention to provide antisense oligonucleotides or oligonucleotide analogs which are capable of inhibiting the function of RNA of influenza viruses.

Yet another object is to provide means for diagnosis of influenza virus types.

These and other objects of this invention will become apparent from a review of the instant specification.

SUMMARY OF THE INVENTION

In accordance with the present invention, oligonucleotides and oligonucleotide analogs are provided which specifically hybridize with RNA's for influenza viruses. The oligonucleotide or oligonucleotide analog is designed to bind directly to influenza RNA in an antisense relationship. The oligonucleotides and oligonucleotide analogs are able to inhibit the function of RNA: either its translation into protein, its translocation into the cytoplasm, or any other activity necessary to its overall biological function. The failure of the RNA to perform all or part of its function results in failure of the portion of the genome controlling the normal life cycle of the virus.

It is preferred to target specific viral RNA for antisense attack. It has been discovered that the genes coding for NP, M1, M2, NS1 and NS2 are particularly useful for this approach. Inhibition of NP, M1, M2, NS1, or NS2 expression is believed to be highly useful for the treatment of influenza viral infections. Such inhibition may also form the basis for diagnostic methods and kits. Inhibition of the genes encoding RNA polymerase, hemagglutinin or neuraminidase of influenza virus is also believed to be highly useful for the treatment of such infections, as is interference with the splicing or packaging functions of the influenza virus RNA, or with the vital nucleoprotein. Such inhibition or interference may also form the basis for diagnostics.

Methods of modulating virus infection comprising contacting the animal with an oligonucleotide or oligonucleotide analog hybridizable with nucleic acids of the virus are provided. Oligonucleotides or analogs hybridizable with RNA from any vRNA segment or from the mRNA's encoding the NP, M1, M2, NS1, or NS2 proteins are preferred.

BRIEF DESCRIPTION OF THE DRAWINGS

FIG. 1 sets forth (+)RNA (mRNA) from influenza virus A (Ann Arbor H2N2), synthesized from segment 5.

FIG. 2 depicts (–)RNA (vRNA) from influenza virus A (Ann Arbor H2N2), from segment 5.

FIG. 3 sets forth (+)RNA (mRNA) from influenza virus A (Ann Arbor H2N2), synthesized from segment 7.

FIG. 4 shows (–)RNA (vRNA) from influenza virus A (Ann Arbor H2N2), from segment 7.

FIG. 5 sets forth (+)RNA (mRNA) from influenza virus A (Ann Arbor H2N2), synthesized from segment 8.

FIG. 6 sets forth (–)RNA (vRNA) from influenza virus A (Ann Arbor H2N2), synthesized from segment 8.

DETAILED DESCRIPTION OF THE INVENTION

Figure 7:
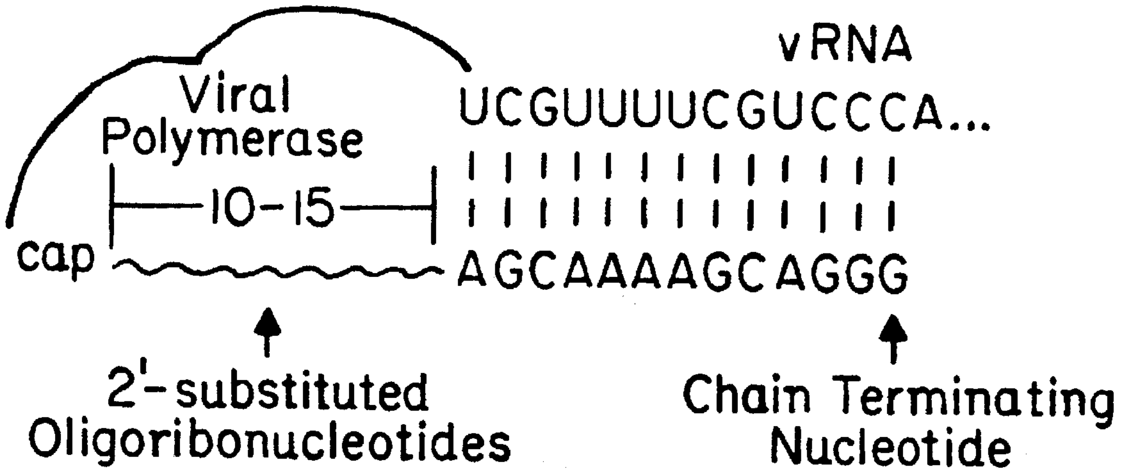
FIG. 7 is a schematic representation depicting the binding of a 2'-substituted oligonucleotide which mimics the cellular RNA primer and inhibits the influenza virus as described in Example 2.

Antisense oligonucleotides hold great promise as therapeutic agents for the treatment of many human diseases. Oligonucleotides specifically bind to the complementary sequence of either pre-mRNA or mature mRNA, as defined by Watson-Crick base pairing, inhibiting the flow of genetic information from DNA to protein. In the case of the influenza viruses, the information to encode proteins lies not in DNA, but in an RNA genome which allows antisense targeting of genomic material. Numerous recent studies have documented the utility of antisense oligonucleotides as biochemical tools for studying target proteins. Rothenberg et al., *J. Natl. Cancer Inst.*, 81:1539–1544 (1989); Zon, G., *Pharmaceutical Res.* 5:539–549 (1988). Because of recent advances in oligonucleotide chemistry, synthesis of nuclease-resistant oligonucleotides, and oligonucleotide analogs which exhibit enhanced cell uptake, it is now possible-to consider the use of antisense oligonucleotides as a novel form of therapeutics.

Influenza viruses are negative strand RNA viruses. Their genome consists of discrete (–)RNA segments, also called vRNA. For example, influenza A consists of 8 segments of (–)RNA. Table 1 is a partial listing of known segments.

TABLE 1

| | INFLUENZA SEGMENTS | |
|---|---|---|
| Segment | Encoded Protein | Virion Location |
| 1 | PB2 RNA Polymerase | Nucleocapsid |
| 2 | PB1 RNA Polymerase | Nucleocapsid |
| 3 | PA RNA Polymerase | Nucleocapsid |
| 4 | HA Hemagglutinin | Envelope |
| 5 | NP Nucleoprotein | Nucleocapsid |
| 6 | NA Neuraminidase | Envelope |
| 7 | M1 Membrane Protein | Envelope |
| | M2 Nonstructural | Not Present |
| 8 | NS1 Nonstructural | Not Present |
| | NS2 Nonstructural | Not Present |

The vRNA segments are the storehouse for the genetic information which serve as the templates for viral mRNA ((+)RNA) synthesis. Thus, in influenza viruses, RNA is used instead of DNA as the transcription templates.

The life cycle of an influenza virus infecting a cell can be summarized. The virus attaches itself to a receptor on the cell surface and is internalized. The vRNA genomic segments inhabit the cell nucleus. The virus brings a number of proteins with it into the newly infected cells including three proteins which make up an RNA-dependent RNA polymerase (PB1, PB2, PA) and a nucleoprotein (NP) which participates with the three RNA polymerase proteins in new RNA synthesis. The virus expresses its genes to make new proteins in the infected cell through the action of the RNA polymerase and nucleoprotein in cooperation with the existing cellular machinery. The virus polymerase does not contain activities to initiate mRNA Synthesis or to cap and methylate the message. These are processes normally required for gene expression. Instead, the virus utilizes a cellular mRNA, cleaving the 5'-capped end of the message approximately 10–15 nucleotides from the cap site and then using it as a primer to initiate its own mRNA synthesis. This unique mechanism is exploited in this invention to achieve specific inhibition of influenza virus.

For therapeutics, an animal suspected of having an influenza virus infection is treated by administering oligonucleotide or oligonucleotide analog in accordance with this invention. Persons of ordinary skill can easily determine optimum dosages, dosing methodologies and repetition rates. Such treatment is generally continued until either a cure is effected or a diminution in the disease state is achieved.

It will be appreciated that species variation among the various influenza viruses occurs. While the various regions are very similar from species to species, some differentiation occurs. Alteration in the oligonucleotides and analogs to account for these variations is specifically contemplated by this invention.

The present invention employs oligonucleotides and oligonucleotide analogs for use in antisense inhibition of the function of influenza virus RNA. In the context of this invention, the term "oligonucleotide" refers to a polynucleotide formed from naturally occurring bases and furanosyl groups joined by native phosphodiester bonds. This term effectively refers to naturally-occurring species or synthetic species formed from naturally-occurring subunits or their close homologs.

"Oligonucleotide analog," as that term is used in connection with this invention, refers to moieties which function similarly to oligonucleotides but which have non-naturally occurring portions. Thus, oligonucleotide analogs may have altered sugar moieties or inter-sugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the ability of the compositions to penetrate into the region of cells where the RNA or DNA whose activity to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with other structures which are, at once, substantially non-ionic and non-chiral, or, in other embodiments, with structures that are chiral and enantiomerically specific. Persons of ordinary skill in the art will be able to select other linkages for use in the practice of the invention.

Oligonucleotide analogs may also include species which include at least some modified base forms. Thus, purines and pyrimidines other than those normally found in nature may be so employed. Similarly, modifications on the pentofuranosyl portions of the nucleotide subunits may also occur as long as the essential tenets of this invention are adhered to.

Such analogs are best described as being functionally interchangeable with natural oligonucleotides (or synthesized oligonucleotides along natural lines), but which have one or more differences from natural structure. All such analogs are comprehended by this invention so long as they function effectively to hybridize with influenza RNA. The oligonucleotides and oligonucleotide analogs in accordance with this invention preferably comprise from about 3 to about 50 subunits. It is more preferred that such oligonucleotides and analogs comprise from about 8 to 25 subunits, and still more preferred to have from about 10 to 20 subunits. As will be appreciated, a subunit is a base-sugar combination suitably bound to adjacent subunits through phosphodiester or other bonds.

The oligonucleotides and analogs used in accordance with this invention may be conveniently and routinely made through the well-known technique of solid phase synthesis. Equipment for such synthesis is sold by several vendors including Applied Biosystems. Any other means for such synthesis may also be employed, however. The actual syntheses of the oligonucleotides are generally within the talents of the routineer. It is also well known to use similar techniques to prepare other oligonucleotide analogs such as the phosphorothioates and alkylated derivatives.

In accordance with this invention, persons of ordinary skill in the art will understand that messenger RNA includes not only the information to encode a protein using the three-letter genetic code, but also associated ribonucleotides which form a region known to such persons as the 5'-untranslated region, the 3'-untranslated region, and intron/exon junction ribonucleotides. Thus, oligonucleotides and oligonucleotide analogs may be formulated in accordance with this invention which are targeted wholly or in part to these associated ribonucleotides as well as to the informational ribonucleotides. In preferred embodiments, the oligonucleotide or analog is specifically hybridizable with a transcription initiation site, a translation initiation site, or an intron/exon junction and sequences in the 3'-untranslated region.

In accordance with this invention, the oligonucleotide is specifically hybridizable with nucleic acids of the influenza virus. In preferred embodiments, said nucleic acids include any of the 8 genomic vRNA segments of influenza A or influenza B or any of the 7 genomic RNA segments from influenza C or corresponding (+)RNA (mRNA) species derived from any of these genes. Oligonucleotides or analogs comprising the corresponding sequence, or part thereof, are useful in the invention. FIG. 1 is the (+)RNA (mRNA) sequence and FIG. 2 is the (–)RNA (vRNA) sequence of the influenza A virus segment 5. FIG. 3 is the (+)RNA (mRNA) sequence and FIG. 4 is the (–)RNA (vRNA) sequence of influenza virus segment 7. FIG. 5 is the (+)RNA (mRNA) sequence and FIG. 6 is the (–)RNA (vRNA) sequence of influenza virus segment 8.

Oligonucleotides and analogs useful in the practice of this invention are complementary to either form of RNA, albeit possibly with somewhat altered mechanism, and are designed to be antisense to one of the RNA sequences or a part thereof, especially one of the sequences relating to segments 5, 7 or 8 relating to the NP, M1, M2, NS1 and NS2 proteins. Useful oligonucleotides and analogs are also designed to be complementary (i.e., antisense) to segments 1, 2, 3, 4, or 6, especially relating to the RNA polymerase, neuraminidase or hemagglutinin proteins, or to RNA sequences important in RNA splicing or viral packaging. Thus, it is preferred to employ any of these oligonucleotides or their analogs, as set forth above or any of the similar nucleotides which persons of ordinary skill in the art can prepare from knowledge of the preferred antisense targets for the modulation of influenza virus infections. Several preferred embodiments of this invention are exemplified in accordance with the following nonlimiting examples. Preferred target genomic and mRNA species for modulation include the NP, M1, M2, NS1 and NS2 protein of influenza virus. Other preferred target RNAs comprise segments 1, 2, 3, 4, or 6, relating to the polymerase 3, polymerase 1, polymerase 2, hemagglutinin, or neuraminidase genes, or splice junctions or packaging sequences. Persons of ordinary skill in the art will appreciate that the present invention is not so limited, however, and that it is generally applicable. The inhibition of these influenza RNAs is expected to have significant therapeutic benefits in the treatment of disease.

EXAMPLES

Example 1

Inhibition of Influenza A Virus, Ann Arbor Strain H2N2

A series of antisense oligonucleotide sequences were selected which are complementary to the Influenza A virus, Ann Arbor strain H2N2. The oligonucleotide sequences selected are complementary to the influenza strain vRNA from segments 5, 7, 8 and mRNA derived from the same segments, which encode the NP protein (segment 5,) M1, M2 proteins (segment 7) and NS1, NS2 proteins (segment 8). A summary of the selected sequences and the precise target regions is shown in Table 2.

TABLE 2

ANTISENSE OLIGONUCLEOTIDES TARGETED TO INFLUENZA TYPE A, ANN ARBOR H2N2

| SEQ. # | SEQUENCE (5' - 3') | | | | | | | TARGET RNA | REGION |
|---|---|---|---|---|---|---|---|---|---|
| 1250 | TTA | TCT | ACC | CTG | CTT | TTG | CT | Segment 5 (+)RNA | Extreme 5' end |
| 1251 | TGG | GAC | GCC | ATG | ATT | TTG | AT | Segment 5 (+)RNA | Initiation of translation |
| 1252 | TTT | GGT | CCC | TTG | GGA | CGC | CA | Segment 5 (+)RNA | Initiation of translation |
| 1253 | GGA | TCC | TTC | CCC | GCG | CTG | GG | Segment 5 (+)RNA | Position 292 |
| 1254 | AGT | AGA | AAC | AAG | GGT | ATT | TT | Segment 5 (+)RNA | Extreme 3' end |
| 1255 | AAA | ATA | CCC | TTG | TTT | CTA | CT | Segment 5 (−)RNA | Extreme 51 end |
| 1256 | TGA | GTG | ACA | TCA | AAA | TCA | TG | Segment 5 (−)RNA | Near 3' end |
| 1257 | AGC | AAA | AGC | AG | GTA | GAT | AA | Segment 5 (−)RNA | Extreme 3' end |
| 1258 | AAT | ATC | TAC | CTG | CTT | TTG | CT | Segment 7 (+)RNA | Extreme 5' end |
| 1259 | TAG | AAG | ACT | CAT | CTT | TCA | AT | Segment 7 (+)RNA | Initiation of translation |
| 1260 | GAG | AGA | ACG | TAC | GTT | TCG | AC | Segment 7 (+)RNA | 5' splice junction |
| 1261 | TCG | GCT | TTG | AG | GGG | CCT | GA | Segment 7 (+)RNA | Position 74 |
| 1262 | CTG | ATA | GGC | CTG | CAA | ATT | TT | Segment 7 (+)RNA | 3' splice junction |
| 1263 | AGT | AGA | AAC | AAG | GTA | GTT | TT | Segment 7 (+)RNA | Extreme 3' end |
| 1264 | AAA | ACT | ACC | TTG | TTT | CTA | CT | Segment 7 (−)RNA | Extreme 5' end |
| 1265 | TCA | GGC | CCC | CTC | AAA | GCC | GA | Segment 7 (−)RNA | Near 3' end |
| 1266 | AGC | AAA | ACC | AGG | TAG | ATA | TT | Segment 7 (−)RNA | Extreme 3' end |
| 1267 | TTT | GTC | ACC | CTG | CTT | TTG | CT | Segment 8 (+)RNA | Extreme 5' end |
| 1268 | GTG | TTA | GGA | TCC | ATT | ATC | TC | Segment 8 (+)RNA | Initiation of translation |
| 1269 | AGC | AAT | CTA | CCT | GAA | AGC | TT | Segment 8 (+)RNA | 5' splice junction |
| 1270 | TAG | TAT | CTC | CTG | GAA | GAG | AA | Segmert 8 (+)RNA | 3' splice junction |
| 1271 | AGT | AGA | AAC | AAG | GGT | GTT | TT | Segment 8 (+)RNA | Extreme 3' end |
| 1272 | AAA | ACA | CCC | TTG | TTT | CTA | CT | Segment 8 (−)RNA | Extreme 5' end |
| 1273 | GCC | TCC | GCA | CCT | GCT | TCG | CG | Segment 8 (−)RNA | Near 3' end |
| 1274 | AGC | AAA | AGC | AGG | GTC | ACA | AA | Segment 8 (−)RNA | Extreme 3' end |

Inhibition of influenza viruses is assayed by standard methods known to those skilled in the art. For example, cells such as the human embryonic lung (MRC5) or Madin-Darby canine kidney (MDCK) lines are readily infected by influenza virus in cell culture. Then cells are grown in culture, rinsed and treated with virus at a multiplicity of infection (M.O.I.) of 0.001–0.01. After allowing for infection, excess virus is washed off and antisense oligonucleotide analog is added at concentrations of 25 to 50 uM, and dilutions thereof. Triplicate wells of virus are used for each dilution. At the end of a treatment time ranging from 5–7 days, the virally infected cells are removed, homogenized and the infection yield of influenza virus is titered by measuring the numbers of plaque produced when dilutions of the extract are plated on a layer of MRC5 cells. A positive drug effect is defined as a reduction in virus yield as a result of drug treatment. A reduction of virus yield of at least about ten fold as compared to the untreated control is expected.

Example 2

RNA Primer Mimics

It is known that transcription of virus-encoded mRNA in influenza-infected cells requires cooperation between the cellular RNA polymerase and viral RNA polymerase. This cooperation is required because the viral RNA polymerase lacks the ability directly to initiate transcription or properly cap and methylate the 5' terminus of mRNA. The viral polymerase complex recruits a cellular mRNA synthesized by the cellular RNA polymerase, cleaves the first 10–15 nucleotides of the cellular mRNA, and uses it to prime its own mRNA transcription; the cellular RNA forms a primer. This unique aspect of viral metabolism provides an opportunity to inhibit the process by antisense oligonucleotides which are complementary to (−)RNA (vRNA) segments at the 3' end, and which extend 10–15 nucleotides further on the 5' side of the antisense oligonucleotide as is depicted generally in FIG. 7.

The antisense oligonucleotides preferred for these embodiments comprise 2'-substituted oligonucleotides, which mimic the structure of RNA and enhance binding to the viral polymerase. It is generally preferred for use in some embodiments of this invention that the 2' position of the linking sugar moieties in at least some of the subunits of the oligonucleotides or oligonucleotide analogs be substituted. Thus, 2' substituents such as OH, SH, F, $OCH_3$, OCN, $O(CH_2)_nCH_3$, where n is from 1 to about 10, and other substituents having similar properties may be useful in some embodiments. The 5' end of the antisense oligonucleotide optionally is capped in a fashion analogous to a typical cellular mRNA or with a cap analog. Some methods for preparing capped oligonucleotides are known to those generally skilled in the art. For example, instructions for preparing some capped oligonucleotides are described by Yisraeli and Melton, *Methods in Enzymology,* 180:42–50 (1989) and references cited therein. Optionally, the 3'end of the antisense oligonucleotide contains a 3' deoxy nucleotide or another nucleotide analog which cannot be extended by RNA polymerase because it lacks a 3' hydroxyl group which is used by the enzyme to extend the RNA chain. The use of such chain-terminating inhibitors is common in many biochemical processes. For example, chain terminating nucleotides are used in sequencing DNA by the method of Sanger. Sanger, F., Nicklen, S., & A. R. Coulson, *Proc. Natl. Acad. Sci.,* 74:5463–5467 (1977). Using this methodology, the following oligonucleotides have been deemed to be good targets for antisense therapeutics and will be synthesized and assayed for antiviral activity as described in Example 1:

UCUCCCUCUCAGAGCGAAAGCAGGTCAAUUAU
UCUCCCUCUCAGAGCGAAAGCAGGCAAACCAU
UCUCCCUCUCAGAGCGAAAGCAGGTACTGATT
UCUCCCUCUCAGCAAAACCUUCCCGGAAAUGA
UCUCCCUCUCAGAGCAAAAGCAGGGUAGAUAA
UCUCCCUCUCAGAGCAAAAGCAGGAGUGAAAA
UCUCCCUCUCAGAGCAAAAGCAGGUAGAUAUU
UCUCCCUCUCAGAGCAAAAGCAGGGUGACAAA

Example 3

Synthesis and Characterization of Oligonucleotides and Analogs

Unmodified DNA oligonucleotides were synthesized on an automated DNA synthesizer (Applied Biosystems model 380B) using standard phosphoramidite chemistry with oxidation by iodine. β-cyanoethyldiisopropylphosphoramidites were purchased from Applied Biosystems (Foster City, Calif.). For phosphorothioate oligonucleotides, the standard oxidation bottle was replaced by a 0.2M solution of 3H-1, 2-benzodithiole-3-one 1,1-dioxide in acetonitrile for the stepwise thiation of the phosphite linkages. The thiation cycle wait step was increased to 68 seconds and was followed by the capping step. 2'-O-methyl phosphorothioate oligonucleotides were synthesized using 2'-O-methyl β-cyanoethyldiisopropylphosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide. After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Tris-borate buffer, pH 7.0. Oligodeoxynucleotides and their phosphorothioate analogs were judged from electrophoresis to be greater than 80% full length material.

The relative amounts of phosphorothioate and phosphodiester linkages obtained by this synthesis were periodically checked by $^{31}P$ NMR spectroscopy. The spectra were obtained at ambient temperature using deuterium oxide or dimethyl sulfoxide-$d_6$ as solvent. Phosphorothioate samples typically contained less than one percent of phosphodiester linkages.

Example 4

Screening of Oligonucleotide Analogs for Ability to Inhibit Virally Induced Cytopathic Effect (CPE)

Antiviral activity of antisense compounds can be rapidly determined by monitoring inhibition of cytopathic effect induced by influenza virus. Since this assay requires microscope examination of the monolayer, it can be carried in microtiter wells, thus reducing the amount of oligonucleotide required for the initial screens. We have used this assay system as a rapid primary screen for antiviral activity.

Influenza virus type A/PR/8/34 was passaged and assayed in pregrown MDCK cell monolayer cultures in Eagles' MEM+2% fetal bovine serum. For the antiviral studies, the virus was diluted in culture medium to yield 32 $CCID_{50}$ (cell culture infectious dose, 50%) per 0.1 ml per culture well.

A total of thirty-two oligonucleotide phosphorothioate analogs were prepared as in Example 3 and stored at −20° C. Just before each use, the compounds were thawed and diluted in culture medium in serial 0.5 $\log_{10}$ concentrations of 20, 6.4, 2.0, 0.6, 0.2 and 0.06 μM.

The known active compound Ribavirin was evaluated concomitantly with the oligonucleotides to serve as a positive control.

MDCK cells were pregrown as monolayers in wells of COSTAR 96-well tissue culture plates, using suitable cell culture medium. The antiviral assays were designed to evaluate six concentrations of each compound in triplicate against the challenge virus. Cell controls containing medium alone, virus-infected cell controls treated only with medium, and uninfected drug cytotoxicity controls (cells and drug) were included in each test plate.

The host cell cultures were pretreated (test wells and drug cytotoxicity controls) with 0.2 ml per well of each drug concentration for 18 hours at 37° C. in a humidified atmosphere containing 2% $CO_2$. Cell culture wells to become virus controls and cell controls were sham-pretreated for 18 hours with experiment medium (MEM+2% fetal bovine serum).

After the 18 hour pretreatment, fluids were removed from the plate wells and the cell monolayers were rinsed with medium. Then each test and virus control culture well was exposed to 0.1 ml of virus suspension for 1 hour at 37° C. Drug toxicity and cell control cultures were sham-infected with 0.1 ml medium per well.

Following the virus adsorption period, fluids were aspirated from the plate wells and the cell monolayers were rinsed with medium to remove any unadsorbed virus. To triplicate virus-infected cultures and to two cytotoxicity control cultures 0.2 ml aliquots of each drug concentration were dispensed. Untreated virus control and cell control cultures were fed with 0.2 ml of experiment medium. The plates were incubated at 37° C. in the $CO_2$ incubator until maximum CPE (cytopathogenic effects) were observed in the virus control cultures (3 days).

The cell culture wells were examined microscopically for CPE and for drug cytotoxicity. Antiviral activity was determined by calculating the degree of inhibition of virus-induced CPE in drug-treated, virus-infected cell cultures by means of a virus rating (VR). The VR is a standard weighted measurement of antiviral activity taking into account both the degree of CPE inhibition and drug cytotoxicity, and is determined by a modification of the method of Ehrlich et al., (Ann. N.Y. *Acad. Sci.* 130:5–16, 1965) as described below. CPE were graded for each individual culture in each microtiter plate well according to the following scale:

4=100% of the cells affected by virus;

3=75% of the cells affected by virus;

2=50% of the cells affected by virus;

1=125% of the cells affected by virus;

0=No CPE; normal cell monolayer u=Unsatisfactory test (contamination/leakage)

t=Drug is toxic to cells; CPE not discernable p=Drug is partially toxic to cells; cell monolayer is intact so that CPE may be discernible.

The VR was calculated as 0.1 of the sum of the numerical differences between the recorded CPE grade of each test well and that of the corresponding virus control in the culture plate. Numerical differences between the scores of test wells containing a drug concentration which was partially cytotoxic (p) and their corresponding virus controls were halved.

In our past experience, we have found that a VR of 1.0 or greater is indicative of significant antiviral activity with a high degree of reproducibility in confirmatory in vitro tests. Therefore, we consider any compound with a VR of 1.0 or greater as active (+). Any compound with a VR of 0.5–0.9 is considered to have possible or marginal activity (±), and any compound with a VR of less than 0.5 is considered to be inactive (–) in our test system.

The minimum inhibitory drug concentration which reduced the CPE by 50% ($MIC_{50}$, or $ID_{50}$) was calculated by using a regression analysis program for semilog curve fitting. A therapeutic index (TI) for each active compound for each susceptible virus was determined by dividing the minimum cytotoxic concentration of the test compound by the $MIC_{50}$.

Initially, phosphorothioate oligonucleotide analogs directed against eight influenza RNA target sites were tested, along with two nonsense controls. The sequences and targets of these oligonucleotide analogs are shown in Table 3.

TABLE 3

Oligonucleotide Analogs Tested for Antivital Activity (all are phosphorothioates)

| SEQ ID NO | ISIS # | Seguence | | | | | | | Target |
|---|---|---|---|---|---|---|---|---|---|
| | 2792 | AGC | AAA | AGC | AGG | GTG | ACA | AA | vRNA, inhibit transcription of segment 8 |
| 2 | 2793 | AGC | GAA | AGC | AGG | TAG | ATA | TT | vRNA, inhibit transcription of segment 7 |
| 3 | 2794 | GTG | TTT | GGA | TCC | ATT | ATG | TC | mRNA, AUG of nonstructural proteins, segment 8 |
| 4 | 2795 | TAG | AAG | ACT | CAT | CTT | TCA | AT | mRNA, AUG of matrix proteins, segment 7 |
| 5 | 2796 | GCA | ATC | TAC | CTG | AAA | GCT | TG | mRNA, splice junction of NS-2, segment 8 |
| 6 | 2797 | AGA | GAA | CGT | ACG | TTT | CTA | CC | mRNA, splice junction of M2, segment 7 |
| 7 | 2798 | AAA | ACA | CCC | TTG | TTT | CTA | CT | vRNA, 5' end packaging sequence, segment 8 |
| 8 | 2799 | AAA | ACT | ACC | TTG | TTT | CTA | CT | vRNA, 5' end packaging sequence, segment 7 |
| 9 | 2800 | GGG | AAA | CCA | ACG | GAA | ATA | AG | Nonsense control oligo |
| 10 | 2801 | CAA | CCA | AAA | AGA | TAA | TCT | CA | Nonsense control oligo |

A summary of the results of the CPE-inhibition assays for these oligonucleotides is given in Table 4.

TABLE 4

Summary of Results of Evaluations of ISIS Compounds for Antiviral Activity Against Influenza Virus Type A/PR/8/34 in MDCK Cell Culture Employing a CPE-Inhibition Assay Procedure

| ISIS # | VR1 | $ID_{50}$[2] (μM) | MTC[3] (μM) | TI[4] |
|---|---|---|---|---|
| 2792 | 1.0 | 13.92 | >20 | >1.43 |
| 2793 | 0 | — | >20 | — |
| 2794 | 1.1 | 12.58 | >20 | >1.59 |
| 2795 | 0.5 | — | >20 | — |
| 2796 | 0.5 | — | >20 | — |
| 2797 | 0.7 | 16.99 | >20 | >1.18 |
| 2798 | 0.7 | 19.98 | >20 | >1.0 |
| 2799 | 0.8 | — | >20 | |
| 2800 | 3.5 | 1.11 | >20 | 17.95 |
| 2801 | 0.4 | — | >20 | — |
| Ribavirin (+ control) | 3.6 | 5.65 μg/ml | 100 μg/ml | 17.69 |

[1]VR = Virus Rating: A measurement of selective antiviral activity which takes into account the degree of inhibition of virus-induced cytopathogenic effects (CPE) and the degree of cytotoxicity produced by the test compound, determined by a modification of the method of Ehrlich et al., Ann. N.Y. Acad. Sci., 130: 5–16 (1965). In our experience, a VR of 1.0 or greater indicates definite (+) antiviral activity, a VR of 0.5–0.9 indicates marginal to moderate (±) antiviral activity, and a VR <0.5 usually indicates no (–) significant antiviral activity.

[2]$ID_{50}$ ($MIC_{50}$) = The minimum drug concentration that inhibited CPE by 50%, calculated by using a regression analysis program for semilog curve fitting.

[3]MTC = The minimum drug concentration causing any cytotoxicity (observed microscopically). Drug cytotoxicity as determined by MTT assay is presented in Table 7.

[4]TI = Therapeutic index, calculated by dividing the minimum cytotoxic drug concentration by the ID50.

Three compounds, ISIS 2792 (SEQ ID NO: 1), ISIS (SEQ ID NO: 3), and ISIS 2800 (SEQ ID NO: 9), had virus ratings of 1.0 or greater; however, the compound with the highest rating (ISIS 2800, SEQ ID NO: 9) was a nonsense control.

A second set of 22 oligonucleotide analogs was then made and tested. The sequences and targets of these oligonucleotides are shown in Table 5.

TABLE 5

Oligonucleotide Analogs Tested for Antiviral Activity (all are phosphorothioates)

| SEQ ID NO: | ISIS # | Sequence | | | | | | | Target |
|---|---|---|---|---|---|---|---|---|---|
| 11 | 3302 | GGG | AAA | CCA | ACG | GAA | ATA | AG | nonsense control |
| 12 | 3303 | CTT | TCC | ATA | TTG | AAT | ATA | AT | AUG segment 1 polymerase 3 |
| 13 | 3304 | ACA | TCC | ATT | CAA | ATG | GTT | TG | AUG segment 2 polymerase 1 |
| 14 | 3305 | TCT | TCC | ATT | TTG | GAT | CAG | TA | AUG segment 3 polymerase 2 |
| 15 | 3306 | GCC | TTC | ATT | TTG | GTT | GTT | TT | AUG segment 4 hemagglutinin |
| 16 | 3307 | GAC | GCC | ATG | ATT | TTG | ATG | TC | AUG segment 5 nucleoprotein |
| 17 | 3308 | GGA | TTC | ATT | TTA | AAC | CCC | TG | AUG segment 6 neuraminidase |
| 18 | 3309 | AGA | CTC | ATC | TTT | CAA | TAT | CT | AUG segment 7 matrix protein |
| 19 | 3310 | GAT | AGA | GAG | AAC | GTA | CGT | TT | left splice junction segment 7 |
| 20 | 3311 | TCT | GAT | AGG | CCT | GCA | AAT | TT | right splice junction segment 7 |
| 21 | 3312 | GGA | TCC | ATT | ATG | TCT | TTG | TC | AUG segment 8 nonstructural protein |
| 22 | 3313 | CAT | GTC | GGT | TAG | GTA | ACG | CG | splice branch segment 8 |
| 23 | 3314 | GCA | ATC | TAC | CTG | AAA | GCT | TG | right splice junction segment 8 |
| 24 | 3315 | AGC | AGT | ATG | TCC | TGG | AAG | AG | left splice junction segment 8 |
| 25 | 3316 | AAA | ACG | ACC | TTG | TTT | CTA | CT | packaging sequence segment 1 |
| 26 | 3317 | AAA | AAT | GCC | TTG | TTC | CTA | CT | packaging sequence segment 2 |
| 27 | 3318 | AAA | AGT | ACC | TTG | TTT | CTA | CT | packaging sequence segment 3 |
| 28 | 3319 | AAA | ACA | CCC | TTG | TTT | CTA | CT | packaging sequence segment 4 |
| 29 | 3320 | AAA | ATA | CCC | TTG | TTT | CTA | CT | packaging sequence segment 5 |
| 30 | 3321 | AAA | AAC | TCC | TTG | TTT | CTA | CT | packaging sequence segment 6 |
| 31 | 3322 | AAA | ACT | ACC | TTG | TTT | CTA | CT | packaging sequence segment 7 |
| 32 | 3323 | AAA | ACA | CCC | TTG | TTT | CTA | CT | packaging sequence segment 8 |

A summary of the results of the CPE-inhibition assays is given in Table 6.

TABLE 6

Summary of Results of Evaluations of ISIS Compounds for Antiviral Activity Against Influenza Virus Type A/PR/8/34 in MDCK Cell Culture Employing a CPE-Inhibition Assay Procedure

| ISIS # | VR1 | $ID_{50}$[2] (μM) | MTC[3] (μM) | TI[4] |
|---|---|---|---|---|
| 3302 | 1.1 | 12.7 | >20 | >1.6 |
| 3303 | 0.8 | 14.7 | >20 | >1.4 |
| 3304 | 0.8 | 17.4 | >20 | >1.2 |
| 3305 | 2.0 | 3.9 | >20 | >5.2 |
| 3306 | 2.6 | 2.0 | >20 | >9.8 |
| 3307 | 3.2 | 1.8 | >20 | >11.4 |
| 3308 | 2.6 | 3.1 | >20 | >6.6 |
| 3309 | 2.1 | 4.5 | >20 | >1.6 |
| 3310 | 1.1 | 12.7 | >20 | >1.6 |
| 3311 | 2.8 | 1.0 | >20 | >19.8 |
| 3312 | 1.6 | 7.0 | >20 | >2.8 |
| 3313 | 2.3 | 3.7 | .20 | >5.5 |
| 3314 | 1.2 | 12.8 | >20 | >1.6 |
| 3315 | 2.6 | 2.1 | >20 | >9.6 |
| 3316 | 1.3 | 8.1 | >20 | >2.5 |
| 3317 | 1.3 | 12.4 | >20 | >1.6 |
| 3318 | 1.2 | 12.7 | >20 | >1.6 |
| 3319 | 3.6 | 0.9 | >20 | >23.5 |
| 3320 | 1.1 | 11.3 | >20 | >1.8 |
| 3321 | 2.7 | 2.4 | >20 | >8.3 |
| 3322 | 2.1 | 2.9 | >20 | >1.4 |
| 3323 | 1.0 | 14.2 | >20 | >1.4 |
| Ribavirin (+ control) | 4.1 | 2.3 μg/ml | 32 μg/ml | 13.9 |
| Ribavirin | 3.9 | 2.6 μg/ml | 32 μg/ml | 12.2 |

[1]VR = Virus Rating: A measurement of selective antiviral activity which takes into account the degree of inhibition of virus-induced cytopathogenic effects (CPE) and the degree of cytotoxicity produced by the test compound, determined by a modification of the method of Ehrlich et al., Ann. N.Y. Acad. Sci., 130: 5–16 (1965). In our experience, a VR of 1.0 or greater indicates definite (+) antiviral activity, a VR of 0.5–0.9 indicates marginal to moderate (±) antiviral activity, and a VR <0.5 usually indicates no (–) significant antiviral activity.

[2]$ID_{50}$ $MIC_{50}$) = The minimum drug concentration that inhibited CPE by 50%, calculated by using a regression analysis program for semilog curve fitting.

[3]MTC = The minimum drug concentration causing any cytotoxicity (observed microscopically). Drug cytotoxicity as determined by MTT assay is presented in Table 8.

[4]TI = Therapeutic index, calculated by dividing the minimum cytotoxic drug concentration by the ID50.

All of the compounds were active against Influenza virus A. Only two compounds, ISIS 3303 (SEQ ID NO: 12) and ISIS 3304 (SEQ ID. NO: 13), had Virus Ratings <1.0. The most active compounds were ISIS 3307 (SEQ ID. NO: 16; VR 3.2) and ISIS 3319 (SEQ ID NO: 28; VR 3.6). The most potency and selectivity were shown by ISIS 3311 (SEQ ID NO: 20; VR 2.8, $ID_{50}$ 1.0 μM, and TI of >19.8) and ISIS 3319 (SEQ ID NO: 28; $ID_{50}$ 0.9 μM and TI of >23.5). The $ID_{50}$'s and TI's were calculated and rounded off to the nearest 0.1. Although the positive control drug Ribavirin appeared to be more active than the test compounds according to the VR, compounds ISIS 3311 (SEQ ID NO: 20) and ISIS 3319 (SEQ ID NO: 28) were more effective against the challenge virus as shown by higher therapeutic indices than the positive control drug.

Example 4

MTT Assay for Oligonucleotide Cytotoxicity

In addition to examining the drug cytotoxicity cell control cultures microscopically for gross morphologic changes, drug cytotoxicity was determined quantitatively by a method utilizing MTT. This method measures cell viability and is based on the reduction of the tetrozolium salt, 3-(4,5-dimethyl-thiazol-2-yl)-2,5-diphenyl tetrazolium bromide (MTT) by mitochondrial enzymes of viable host cells to MTT formazan, T. Mossmann, *J. Immunol. Methods.*, 65: 55, 1983. Drug cytotoxicity controls and cell controls were treated with MTT followed by SDS to dissolve the crystals of MTT formazan. The blue color of the MTT formazan was measured spectrophotometrically at 570 nm on an automated plate reader. Drug cytotoxicity (viability) was determined by comparing the absorbance (optical density, O.D.) of each drug cytotoxicity control with the mean O.D. of the cell control with the mean O.D. of the cell control cultures and expressed as percent of control.

None of the 32 compounds was toxic at 20 μM, the highest dose evaluated, by microscopic evaluation (Tables 4 and 6) or by MTT assay (Tables 7 and 8).

TABLE 7

Viability[1] of Drug-Treated MDCK Cell Control Cultures As Determined by MTT Assay

| Compound | Percent of Control | | | | | |
|---|---|---|---|---|---|---|
| No. | 20 μM | 6.4 μM | 2.0 μM | 0.64 μM | 0.2 μM | 0.06 μM |
| 2792 | 96 | 99 | 97 | 96 | 93 | 91 |
| 2793 | 98 | 100 | 96 | 96 | 92 | 91 |
| 2794 | >100 | >100 | >100 | >100 | 96 | 93 |
| 2795 | >100 | 99 | >100 | 98 | 91 | 90 |
| 2796 | 97 | >100 | 99 | 94 | 91 | 91 |
| 2797 | 98 | 99 | 98 | 94 | 90 | 91 |
| 2798 | 94 | 98 | 97 | 96 | 89 | 89 |
| 2799 | 96 | 99 | >100 | 98 | 93 | 93 |
| 2800 | >100 | 99 | 100 | 93 | 94 | 92 |
| 2801 | 98 | >100 | 100 | 98 | 92 | 93 |
| | 320 μg/ml | 100 μg/ml | 32 μg/ml | 10 μg/ml | 3.2 μg/ml | 1.0 μ/ml |
| Ribavirin | 56 | 58 | 63 | 78 | 86 | 94 |

[1]Viability (drug cytotoxicity) determined by comparing the absorbance (optical density, OD) of each drug cytotoxicity control with the mean OD of the untreated cell control cultures and expressed as percent of control.

TABLE 8

Viability[1] of Drug-Treated MDCK Cell Control Cultures As Determined by MTT Assay

| Compound | Percent of Control | | | | | |
|---|---|---|---|---|---|---|
| No. | 20 μM | 6.4 μM | 2.0 μM | 0.64 μM | 0.2 μM | 0.06 μM |
| 3302 | 100 | 100 | 100 | 99 | 91 | 94 |
| 2202 | 100 | 100 | 100 | 96 | 93 | 89 |
| 3304 | 100 | 100 | 100 | 100 | 95 | 91 |
| 3305 | 97 | 100 | 100 | 99 | 96 | 92 |
| 3306 | 100 | 100 | 100 | 100 | 98 | 97 |
| 3307 | 95 | 100 | 100 | 100 | 100 | 100 |
| 3308 | 98 | 97 | 95 | 96 | 93 | 93 |
| 3309 | 96 | 93 | 97 | 94 | 93 | 96 |
| 3310 | 96 | 95 | 92 | 93 | 88 | 91 |
| 3311 | 90 | 88 | 89 | 92 | 92 | 93 |
| 3312 | 95 | 93 | 93 | 93 | 90 | 94 |
| 3313 | 96 | 97 | 96 | 96 | 94 | 92 |
| 3314 | 89 | 95 | 98 | 97 | 94 | 93 |
| 3315 | 89 | 95 | 95 | 96 | 97 | 93 |
| 3316 | 90 | 95 | 93 | 92 | 91 | 89 |
| 3317 | 94 | 92 | 93 | 91 | 91 | 89 |
| 3318 | 93 | 97 | 93 | 93 | 90 | 91 |
| 3319 | 94 | 99 | 97 | 99 | 97 | 97 |
| 3320 | 95 | 100 | 100 | 100 | 96 | 93 |
| 3321 | 98 | 98 | 99 | 97 | 99 | 92 |
| 3322 | 98 | 99 | 100 | 99 | 96 | 91 |

TABLE 8-continued

| Viability[1] of Drug-Treated MDCK Cell Control Cultures As Determined by MTT Assay | | | | | | |
|---|---|---|---|---|---|---|
| 3323 | 100 | 100 | 100 | 100 | 99 | 100 |
| | 320 μg/ml | 100 μg/ml | 32 μg/ml | 10 μg/ml | 3.2 μg/ml | 1.0 μ/ml |
| Ribavirin | 35 | 52 | 52 | 80 | 98 | 96 |
| Ribavirin | 37 | 55 | 57 | 83 | 97 | 96 |

[1]Viability (drug cytotoxicity) determined by comparing the absorbance (optical density, OD) of each drug cytotoxicity control with the mean OD of the untreated cell control cultures and expressed as percent of control.

The selectivity of these active materials may therefore be greater than demonstrated by these assays.

Example 5

RNA Mimicry to Inhibit Virion Assembly

One of the important aspects of the influenza life cycle is virion assembly. In this process the virus needs to select one of each of the eight unique viral RNA (vRNA) segments for packaging into a complete (infectious) virion. Recognition of the vRNA segments by viral proteins is an essential component of this process. The 5' end of the vRNA segments has been identified as the binding site(s) for viral protein(s). The ribonucleotide sequence at the 5' end of the vRNA segments is conserved throughout the eight segments, as shown in Table 9:

TABLE 9

| (Sequence shown is from influenza A/PR/8/34; First 30 nucleotides are shown) | |
|---|---|
| SEG1 | AGCGAAAGCAGGTCAATTATATTCAATATG |
| SEG2 | AGCGAAAGCAGGCAAACCATTTGAATGGAT |
| SEG3 | AGCGAAAGCAGGTACTGATCCAAAATGGAA |
| SEG4 | AGCAAAAGCAGGGGAAAATAAAAACAACCA |
| SEG5 | AGCAAAAGCAGGGTAGATAATCACTCACTG |
| SEG6 | AGCGAAAGCAGGGGTTTAAAATGAATCCAA |
| SEG7 | AGCGAAAGCAGGTAGATATTGAAAGATGAG |
| SEG8 | AGCAAAAGCAGGGTGACAAAGACATAATGG |

Moreover, these sequences are highly conserved among different strains of influenza virus.

As can be seen from these sequences, the first 12 bases are highly conserved in each of the 8 segments. Therefore, an oligonucleotide targeting this conserved region (e.g., SEQ ID NO: 33) should be effective.

Analysis of the potential RNA secondary structures of the 5' ends of the influenza vRNAs suggests that there is a strong secondary structure at the end of each segment which may play an important role in protein recognition. As disclosed in U.S. patent application Ser. No.: 497,090, filed Mar. 21, 1990, and PCT/US91/01822, filed Mar. 19, 1991, each of which is assigned to the assignee of the present invention and incorporated by reference herein, the interaction of certain RNAs with proteins may be inhibited through employment of oligonucleotides or oligonucleotide analogs which mimic at least a portion of the RNA. This is thought to be particularly effective when said RNA has a strong secondary structure that can be exploited through RNA mimicry. Gene expression and the maintenance of disease states can be interfered with through interference with such RNA-protein interactions. It is not necessary to know the actual RNA structure in order to practice this invention, it is only necessary to know that a specific RNA sequence is recognized by an RNA-binding protein and that this interaction has important biological consequences.

The RNA mimetic oligonucleotides shown in Table 10 will be synthesized as uniform 2'-O-methyl or 2'-O-methyl phosphorothioate analogs as described in Example 3, and will be screened for antiviral activity as described in Example 4.

What is claimed is:

1. An oligonucleotide having SEQ ID NO: 1, SEQ ID NO: 3, SEQ ID NO: 4, SEQ ID NO: 5, SEQ ID NO: 6, SEQ ID NO: 7 or SEQ ID NO: 8, wherein at least some of the internucleotide linkages within said oligonucleotide are phosphorothioate linkages.

2. An oligonucleotide having SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31 or SEQ ID NO: 32 SEQ., wherein at least some of the internucleotide linkages within said oligonucleotide are phosphorothioate linkages.

3. A method of inhibiting influenza virus replication in cells in vitro by introducing an oligonucleotide having SEQ ID NO: 1, SEQ ID NO: 3, SEQ ID NO: 4, SEQ ID NO: 5, SEQ ID NO: 6, SEQ ID NO: 7 or SEQ ID NO: 8, wherein at least some of the internucleotide linkages within said oligonucleotide are phosphorothioate linkages, into said cells in an amount sufficient to inhibit replication.

4. A method of inhibiting influenza virus replication in cells in vitro by introducing an oligonucleotide having SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31 or SEQ ID NO: 32 SEQ., wherein at least some of the internucleotide linkages within said oligonucleotide are phosphorothioate linkages, into said cells in an amount sufficient to inhibit replication.

* * * * *

UNITED STATES PATENT AND TRADEMARK OFFICE

CERTIFICATE OF CORRECTION

PATENT NO. : 5,580,767

DATED : December 3, 1996

INVENTOR(S) : Cowsert et al.

It is certified that error appears in the above-indentified patent and that said Letters Patent is hereby corrected as shown below:

Column 1, line 34, please delete "Shops" and insert therefor --Shope--

Column 4, line 19, after "possible" and before "to", please delete the dash

Columns 7 and 8, Table 2, row 1255, after "(-)RNA", please delete "Extreme 51 end" and insert therefor --Extreme 5' end--

Columns 11 and 12, Table 3, after "ISIS #", please delete "Seguence" and insert therefor "Sequence"

Columns 11 and 12, Table 4, after "VR1" please delete "$ID_{50}{}^{2}$" and insert therefor --$ID^{2}{}_{50}$-- at all three locations Column 12, Table 4, row 2799, after ">20", please insert a dash in the last column Column 12, line 63, after "ISIS" and before "(SEQ ID NO: 3)", please insert -- 2794--

Column 15, Table 6, after "VR1" please delete "$ID_{50}{}^{2}$" and insert therefor --$ID^{2}{}_{50}$--

Column 16, line 51, Table 8, please delete "2202" and insert therefor, --3303--

Column 18, line 41 insert Table 10 as shown on the attached page.

UNITED STATES PATENT AND TRADEMARK OFFICE
CERTIFICATE OF CORRECTION

PATENT NO. : 5,580,767

DATED : December 3, 1996

INVENTOR(S) : Cowsert et al.

It is certified that error appears in the above-indentified patent and that said Letters Patent is hereby corrected as shown below:

TABLE 10

| SEQ ID NO: | |
|---|---|
| 34 | AGCGAAAGCAGGTCAATTATATTCAATATG |
| 35 | AGCGAAAGCAGGCAAACCATTTGAATGGAT |
| 36 | AGCGAAAGCAGGTACTGATCCAAAATGGAA |
| 37 | AGCAAAAGCAGGGGAAAATAAAAACAACCA |
| 38 | AGCAAAAGCAGGGTAGATAATCACTCACTG |
| 39 | AGCGAAAGCAGGGGTTTAAAATGAATCCAA |
| 40 | AGCGAAAGCAGGTAGATATTGAAAGATGAG |
| 41 | AGCAAAAGCAGGGTGACAAAGACATAATGG |

Signed and Sealed this

First Day of July, 1997

Attest:

BRUCE LEHMAN

*Attesting Officer* *Commissioner of Patents and Trademarks*

SEQUENCE LISTING ( 1 ) GENERAL INFORMATION:

( i i i ) NUMBER OF SEQUENCES: 41

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:1:

AGCAAAAGCA GGGTGACAAA 20

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:2:

AGCGAAAGCA GGTAGATATT 20

( 2 ) INFORMATION FOR SEQ ID NO:3:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:3:

GTGTTTGGAT CCATTATGTC 20

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:4:

TAGAAGACTC ATCTTTCAAT 20

( 2 ) INFORMATION FOR SEQ ID NO:5:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:5:

GCAATCTACC TGAAAGCTTG 20

( 2 ) INFORMATION FOR SEQ ID NO:6:

( i ) SEQUENCE CHARACTERISTICS:
( A ) LENGTH: 20 base pairs
( B ) TYPE: nucleic acid
( C ) STRANDEDNESS: single -continued ( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:6:

AGAGAACGTA CGTTTCTACC 20

( 2 ) INFORMATION FOR SEQ ID NO:7:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:7:

AAAACACCCT TGTTTCTACT 20

( 2 ) INFORMATION FOR SEQ ID NO:8:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:8:

AAAACTACCT TGTTTCTACT 20

( 2 ) INFORMATION FOR SEQ ID NO:9:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:9:

GGGAAACCAA CGGAAATAAG 20

( 2 ) INFORMATION FOR SEQ ID NO:10:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:10:

C A A C C A A A A A   G A T A A T C T C A   2 0

( 2 ) INFORMATION FOR SEQ ID NO:11:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:11:

G G G A A A C C A A   C G G A A A T A A G   2 0

( 2 ) INFORMATION FOR SEQ ID NO:12:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:12:

C T T T C C A T A T   T G A A T A T A A T   2 0

( 2 ) INFORMATION FOR SEQ ID NO:13:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:13:

A C A T C C A T T C   A A A T G G T T T G   2 0

( 2 ) INFORMATION FOR SEQ ID NO:14:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES -continued ( x i ) SEQUENCE DESCRIPTION: SEQ ID NO:14:

TCTTCCATTT TGGATCAGTA 20

( 2 ) INFORMATION FOR SEQ ID NO:15:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:15:

GCCTTCATTT TGGTTGTTTT 20

( 2 ) INFORMATION FOR SEQ ID NO:16:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:16:

GACGCCATGA TTTTGATGTC 20

( 2 ) INFORMATION FOR SEQ ID NO:17:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:17:

GGATTCATTT TAAACCCCTG 20

( 2 ) INFORMATION FOR SEQ ID NO:18:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:18:

AGACTCATCT TTCAATATCT 20

-continued ( 2 ) INFORMATION FOR SEQ ID NO:19:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:19:

GATAGAGAGA ACGTACGTTT 20

( 2 ) INFORMATION FOR SEQ ID NO:20:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:20:

TCTGATAGGC CTGCAAATTT 20

( 2 ) INFORMATION FOR SEQ ID NO:21:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:21:

GGATCCATTA TGTCTTTGTC 20

( 2 ) INFORMATION FOR SEQ ID NO:22:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:22:

CATGTCGGTT AGGTAACGCG 20

( 2 ) INFORMATION FOR SEQ ID NO:23:

( i ) SEQUENCE CHARACTERISTICS:

( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:23:

G C A A T C T A C C   T G A A A G C T T G   2 0

( 2 ) INFORMATION FOR SEQ ID NO:24:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:24:

A G C A G T A T G T   C C T G G A A G A G   2 0

( 2 ) INFORMATION FOR SEQ ID NO:25:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:25:

A A A A C G A C C T   T G T T T C T A C T   2 0

( 2 ) INFORMATION FOR SEQ ID NO:26:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:26:

A A A A A T G C C T   T G T T C C T A C T   2 0

( 2 ) INFORMATION FOR SEQ ID NO:27:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:27:

AAAAGTACCT TGTTTCTACT 20

( 2 ) INFORMATION FOR SEQ ID NO:28:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:28:

AAAACACCCT TGTTTCTACT 20

( 2 ) INFORMATION FOR SEQ ID NO:29:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i i ) HYPOTHETICAL: NO ( i v ) ANTI-SENSE: YES ( x i ) SEQUENCE DESCRIPTION: SEQ ID NO:29:

AAAATACCCT TGTTTCTACT 20

( 2 ) INFORMATION FOR SEQ ID NO:30:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:30:

AAAAACTCCT TGTTTCTACT 20

( 2 ) INFORMATION FOR SEQ ID NO:31:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES -continued ( x i ) SEQUENCE DESCRIPTION: SEQ ID NO:31:

AAAACTACCT TGTTTCTACT 20

( 2 ) INFORMATION FOR SEQ ID NO:32:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: YES ( x i ) SEQUENCE DESCRIPTION: SEQ ID NO:32:

AAAACACCCT TGTTTCTACT 20

( 2 ) INFORMATION FOR SEQ ID NO:33:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:33:

AGCRAAAGCA GG 12

( 2 ) INFORMATION FOR SEQ ID NO:34:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:34:

AGCGAAAGCA GGTCAATTAT ATTCAATATG 30

( 2 ) INFORMATION FOR SEQ ID NO:35:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:35:

AGCGAAAGCA GGCAAACCAT TTGAATGGAT 30

-continued ( 2 ) INFORMATION FOR SEQ ID NO:36:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:36:

AGCGAAAGCA GGTACTGATC CAAAATGGAA 30

( 2 ) INFORMATION FOR SEQ ID NO:37:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:37:

AGCAAAAGCA GGGGAAAATA AAAACAACCA 30

( 2 ) INFORMATION FOR SEQ ID NO:38:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:38:

AGCAAAAGCA GGGTAGATAA TCACTCACTG 30

( 2 ) INFORMATION FOR SEQ ID NO:39:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:39:

AGCGAAAGCA GGGGTTTAAA ATGAATCCAA 30

( 2 ) INFORMATION FOR SEQ ID NO:40:

-continued ( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:40:

AGCGAAAGCA GGTAGATATT GAAAGATGAG 30

( 2 ) INFORMATION FOR SEQ ID NO:41:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:41:

AGCAAAAGCA GGGTGACAAA GACATAATGG 30